United States Patent [19]
Kushner et al.

[11] Patent Number: 5,221,410
[45] Date of Patent: Jun. 22, 1993

[54] CRYSTAL FORMING DEVICE

[75] Inventors: Harold K. Kushner, West Orange; Paul Reichert, Montville; Henry R. Sochon, Clifton, all of N.J.

[73] Assignee: Schering Corporation, Kenilworth, N.J.

[21] Appl. No.: 774,766

[22] Filed: Oct. 9, 1991

[51] Int. Cl.$^5$ ............................................. C30B 35/00
[52] U.S. Cl. .................................... 156/600; 156/621; 156/DIG. 62; 156/DIG. 90; 156/DIG. 113; 422/248
[58] Field of Search ............... 156/600, 621, DIG. 62, 156/DIG. 90, DIG. 113; 422/248

[56] References Cited

U.S. PATENT DOCUMENTS

| | | |
|---|---|---|
| 2,561,339 | 7/1951 | Chediak . |
| 3,055,808 | 9/1962 | Henderson . |
| 3,107,204 | 10/1963 | Brown et al. . |
| 3,165,450 | 1/1965 | Scheidt . |
| 4,012,288 | 3/1977 | Lyman et al. ............ 195/139 |
| 4,299,921 | 11/1981 | Youssef ................... 435/298 |
| 4,599,314 | 7/1986 | Shami ..................... 435/287 |
| 4,599,315 | 7/1986 | Terasaki et al. ......... 435/301 |
| 4,682,891 | 7/1987 | de Macario et al. ..... 356/244 |
| 4,770,856 | 9/1988 | Uthermann et al. ..... 422/104 |
| 4,822,741 | 4/1989 | Banes ...................... 435/300 |
| 4,886,646 | 12/1989 | Carter et al. ............. 156/DIG. 62 |
| 5,096,676 | 3/1992 | McPherson et al. ..... 156/DIG. 62 |

OTHER PUBLICATIONS

A. McPherson, Preparation and Analysis of Protein Crystals, John Wiley & Sons, N.Y., N.Y., pp. 82–127, 1982.
F. R. Salemme, Arch. Biochem. Biophys., "A Free Interface Diffusion Technique for the Crystallization of Proteins for X-ray Crystallography", vol. 151, pp. 533–539, 1972.
K. Bailey, Nature, vol. 145, N. 3685, pp. 934–935, Jun. 15, 1940.
R. H. Davies et al, Methods in Enzymology, "Enzyme Purification and Related Techniques", vol. 21, pp. 266–299, 1971.
N. D. Jones et al, Annual Meeting of American Crystallographic Assoc., p. 27, 1987.
K. B. Ward et al, J. Crystal Growth, "Automatic Preparation of Protein Crystals Using Laboratory Robotics and Automated Visual Inspection," vol. 90, pp. 325–339, 1988.
K. B. Ward et al, LRA, "Preparation of Protein Crystals Using Robotics and Automated Visual Inspection," vol. 1, pp. 157–176, 1988.
D. Morris et al, Biotechniques, "Automation of Protein Crystallization Trials": Use of a Robot to Deliver Reagents to a Novel Multi-chamber Vapor Diffusion Plate, vol. 7, #5, 1989.
M. L. Pusey et al, The Journal of Biological Chemistry, "Protein Crystal Growth, Growth Kinetics for Tetragonal Lysozyme Crystals", vol. 261, No. 14, pp. 6524–6529, May 15, 1986.

*Primary Examiner*—Robert Kunemund
*Assistant Examiner*—Felisa Garrett
*Attorney, Agent, or Firm*—Norman C. Dulak

[57] ABSTRACT

A crystal forming device includes a base plate having a plurality of wells therein, each well adapted to receive a reservoir solution therein and each well having a bottom and a circumferential side wall connected with the bottom to define a chamber therein, the side wall having an upper circumferential edge defining an upper opening of the well; a single removable cover for covering all of the wells, the single removable cover having a lower surface which rests on the upper circumferential edges of the wells to seal the wells and to thereby seal the chambers, the cover having a plurality of circular beads formed on the lower surface thereof, the circular beads corresponding in position to the upper circumferential edges of the wells and the circular beads extending in surrounding relation to respective the upper circumferential edges when the cover is positioned on the base plate; and a silicon grease applied to the upper circumferential edges for sealing the lower surface of the single removable cover to each the well to define a plurality of sealed crystallization chambers.

6 Claims, 2 Drawing Sheets

CRYSTAL FORMING DEVICE

BACKGROUND OF THE INVENTION

The present invention relates generally to crystallization chambers, and more particularly, is directed to a device for forming crystals with vapor diffusion in the hanging drop method.

Supersaturated solutions of macromolecules (such as proteins and nucleic acids) and peptides under conditions of defined pH, temperature and precipitant levels form crystals. Macromolecular crystals have been used in the biotechnology-pharmaceutical industry for many purposes. For example, three-dimensional models of macromolecule structures derived from X-ray diffraction analysis of crystals are used to design new drugs in pharmaceutical research. As another example, crystallization steps are utilized in purification-manufacturing processes of biotechnology-derived products. Further, crystalline complexes such as zinc-insulin are used for controlled release drug formulations.

It is necessary, however, to produce the correct conditions for macromolecular crystallization. This requires screening a wide range of conditions. See, for example, A. McPherson, *Preparation and Analysis of Protein Crystals*, John Wiley and Sons, New York, N.Y., pages 82-127, 1982.

Various microtechniques are presently used to discover conditions for macromolecule crystallization, including, for example, the free interface diffusion method (see F. R. Salemme, Arch. Biochem. Biophys., pages 151 and 533, 1972), vapor diffusion in the hanging or sitting drop method (see A. McPherson, *Preparation and Analysis of Protein Crystals*, John Wiley and Sons, New York, N.Y., pages 96-97, 1982), and liquid dialysis (see K. Bailey, Nature, pages 145 and 934, 1940).

Of the presently used methods, vapor diffusion is the most commonly used method for growing macromolecular crystals from solution, and the most common technique used for screening conditions for crystallization is vapor diffusion in the hanging drop method. See R. H. Davies and D. M. Segal, *Methods in Enzymology*. Academic Press, New York, N.Y., Vol. 22, page 266, 1971. The vapor diffusion method has advantages over other crystallization methods because it is truly a micro-crystallization technique. Vapor diffusion in the hanging drop technique allows screening of a large range of conditions while utilizing a relatively small amount of macromolecule or peptide.

For the formation of crystals from a protein, the vapor diffusion hanging droplet method is known. Specifically, a droplet containing a macromolecular solution is suspended in a sealed chamber. The macromolecular solution in the droplet is allowed to equilibrate with a reservoir containing a higher concentration of precipitating agent. Over time, water vapor diffuses from the less concentrated macromolecular solution to the more concentrated reservoir solution and slowly increases the concentration of macromolecule and precipitating agent within the droplet.

As an example, in a sealed (gas and vapor impermeable) chamber, a reservoir of, for example, 1 ml of 10% saturated ammonium sulphate, is provided. On the inside wall of the cover of the system, a 10 $\mu$l protein droplet of, for example, 5% saturated ammonium sulphate, is provided. Because of the difference in vapor pressure between the droplet and the reservoir, water will evaporate from the droplet until an equilibrium results. Thus, the droplet may shrink, for example, 50% from 10 $\mu$l to 5 $\mu$l, so that a crystal will form.

In particular, vapor diffusion in hanging drop experiments are typically performed in 24 well tissue culture plates of the type sold by Linbro Flow Laboratories of McLean, Va. (Linbro Tissue Culture Multiwell Plate/Cover, Catalog No. 76-033-05) and Becton Dickinson and Company of Lincoln Park, N.J. (under the trademark FALCON 3047 MULTIWELL). The reservoir solutions are placed within each of the 24 wells of the tissue culture plate. The rim of each well is then greased with a silicon grease, such as a high vacuum grease sold by Dow Corning Corporation of Midland, Mich. Micro coverglasses or cover slips, for example, having a No. 2 thickness and an 18 mm diameter, are siliconized with siliconizing agents, such as a siliconizing agent sold under the trademark SURFASIL by Pierce Chemical Company of Rockford, Ill. A 1–40 $\mu$l droplet containing a concentrated buffered solution of a homogeneous macromolecule and a precipitating agent, such as saturated ammonium sulfate, polyethylene glycol polymer, or a low molecular weight alcohol or solvent, is dispensed on each siliconized coverglass. The coverglasses are then inverted over the greased wells of the tissue culture plate and sealed by the silicon grease thereon. Typically, several components, such as buffers, salts, macromolecule concentration and precipitating agents, of both the droplet and reservoir solution in the wells are systematically varied, as well as conditions of vapor pressure, temperature, concentrations and the like.

With the coverglasses inverted, each droplet hangs down from its respective coverglass over or adjacent to the respective reservoir. Each experiment is generally allowed to equilibrate under 4° C. or 22° C. incubation conditions, and is monitored microscopically for crystal growth over various time intervals, for example, 3 days, 7 days, 1 month and 3 months, although other time intervals can be used.

Typically, several thousand experiments must be performed before conditions are found to produce high quality crystals. In this regard, it is noted that the setup of vapor diffusion hanging drop experiments is a very labor-intensive process which must be performed by experienced technical personnel. For example, multiple aspirating and dispensing steps of components, multiple greasing and polishing steps and the like must be performed in the experimental setup. Further, for each well, a separate cover slip must be manually inverted thereover. The volume and complexity of steps can produce a wide variation in experimental results. Still further, manpower restraints usually limit the range of conditions screened for crystallization.

For the above mentioned reasons, several research groups have developed their own automated crystallization systems.

The first robotic crystallization system based on the hanging drop method has been commercially available since 1987 from ICN Biomedicals. The system is a computer controlled sample preparation system, including a color monitor, a printer and a menu driven computer program. The system utilizes a 24 well multiwell plate and performs all of the required aspirating and dispensing steps of a classical coverglass-multiwell plate hanging drop setup. Specifically, the system includes means to automatically pipette reservoir solution into the wells, and to automatically pipette droplets onto the coverglasses or cover slips. However, this system requires full time intervention of a technician to manipulate the dispensed droplets on coverglasses over the corresponding wells. In other words, the technician must still manually apply silicon grease to the rim of each well, and then invert each coverglass over its respective well. This, of course, is time-consuming and burdensome.

A second approach to automated crystallization was developed at Lilly Research Laboratories in Indianapolis, Ind. in collaboration with the U.S. Naval Institute, and has been designated "APOCALYPSE", a fully automated system. See N. D. Jones et al, Annual Meeting of the American Crystallographic Association, page 27, 1987, and K. B. Ward et al, J. Crystal Growth, pages 90 and 325, 1988. The system utilizes a robot sold by Zymark Corporation under the trademark ZYMATE II, and a Master Laboratory pipetting station. In addition, the system uses a specially designed plate sold by Flow Laboratories under the trademark CRYSTALPLATE. The plate has a 3×5 array of wells for crystallization experiments. Each crystallization well has two coverglasses and two oil troughs to be filled. Specifically, there is a lower square-shaped oil trough surrounding a lower opening and an upper square-shaped oil trough surrounding an upper opening, the upper oil trough being larger than the lower oil trough. One coverglass is positioned over the lower oil trough so as to seal the lower opening and another coverglass is positioned over the upper oil trough so as to seal the upper opening. As a result, a sealed chamber is formed between the upper and lower coverglasses. A reservoir is formed adjacent the oil troughs and is in gaseous communication with the sealed chamber.

However, numerous operations are required to set up and seal each well. Specifically, oil must first be dispensed into each trough. Then, the reservoir must be filled. The lower cover slip is then positioned over the lower oil trough so as to seal the lower opening. A droplet is then deposited on the upper cover slip, which is subsequently inverted and positioned over the upper oil trough.

This specially designed plate has several advantages over the aforementioned classical coverglass-tissue culture plate set-up. First, the plate can be readily handled by a forklift hand of an articulated robotic arm such as the Zymark robot. The plate also has excellent optical visualization properties since the droplet is not viewed through a reservoir, that is, the reservoir is adjacent the droplet rather than beneath it. In addition, the plate can accommodate either hanging (from the upper coverglass), sitting (on the lower coverglass) or sandwiched (in contact with both coverglasses) drops.

However, the plate has many disadvantages. In the first place, there are cumbersome multiple coverglasses to be handled. Further, because the plate uses an oil trough to seal each well of, the coverglass-crystallization chamber, additional time must be spent ensuring the correct height of the oil in the troughs. In other words, the height of the oil has to be precise in order to obtain a meniscus which will ensure sealing of the coverglasses. For example, if the oil height is too low, there will be no seal. On the other hand, if the oil height is too high, the oil from the upper oil trough will run into the reservoir and/or lower oil trough, and the oil from the lower oil trough will run into the reservoir. Still further, the plate has a relatively slow equilibration rate compared to comparable classical coverglass-multiwell plate experiments. Lastly, conditions for crystallizing macromolecules in this plate have been found to be considerably different from conventional hanging drop experiments.

A third approach to automated crystallization has been developed by Cryschem Corporation using the "Biomek" automated liquid handling system. See D. Morris et al, Biotechniques, Vol. 7, No. 5, 1989. With this approach, a specially designed plate was developed and sold under the designation MD/24 for use in this automated system. The plate has 24 wells, each well having a center post or tee for standing drops and each well being surrounded by the reservoir at a slightly lower level than the center post but in gaseous communication therewith. In order to provide the sealed chambers, a clear mylar film from Corning Glass Co. is sealed over the plate. Thus, there is no coverglass manipulation involved in setting up experiments. Droplets are dispensed directly on the center tee and subsequently sealed with the mylar film.

There are several disadvantages with the MD/24 plate. First, the mylar film has poor optical properties. Further, in order to view experiments, the mylar film must be peeled away. This disturbs the on-going vapor equilibration process. Also, after several microscopic inspections, the mylar film can no longer maintain a good seal in all the wells. These problems have inhibited wide use of the MD/24 chamber for routine screening.

In addition, various U.S. patents show and/or disclose related structures.

For example, U.S. Pat. No. 3,107,204 to Brown et al discloses a microbiological testing method and structure therefor. Specifically, the patent discloses a tray having a plurality of wells therein, and a cover for covering the tray. The cover is sealed to the tray around the outer periphery, and importantly, also includes projections which tightly fit within the wells so as to individually seal the same. There is no indication that there is a gaseous seal of the wells. Further, there is a snap-fitting or tight connecting seal between the cover and tray, which would make it difficult to use the same as a crystallization chamber in connection with the vapor diffusion hanging drop method for forming macromolecular crystals.

U.S. Pat. No. 3,165,450 to Scheidt discloses an anaerobic culturing device formed by a shallow dish having partitions which partition the dish into four quadrants. The partitions are of a height lower than the outer wall of the dish. Thus, even when the cover is sealed to the dish, the chambers formed by the partitions are in open gaseous communication with each other. Therefore, this device could not be used to form individual sealed chambers of a crystallization chamber. See also U.S. Pat. No. 3,055,808 to Henderson which is similar and suffers from the same deficiencies.

U.S. Pat. No. 2,561,339 to Chediak discloses a similar arrangement, and it is clear that the wells are in open communication with each other. See also U.S. Pat. No. 4,822,741 to Banes.

U.S. Pat. No. 4,770,856 to Uthemann et al discloses an arrangement in which the tray has a plurality of wells. The tray or plate has a peripheral ledge on which the cover rests. Therefore, this arrangement is similar to the FALCON 3047 MULTIWELL tissue culture plate of Becton-Dickinson and Co., and is deficient for the same reasons for use as a crystallization chamber. See also the prior art description in FIGS. 2 and 3B of U.S. Pat. No. 4,682,891 to de Macario et al.

U.S. Pat. No. 4,012,288 to Lyman et al discloses a tissue culture cluster dish which is similar to the FALCON 3047 MULTIWELL plate by Becton-Dickinson and Co. Although the upper ends of the well walls extend above the upper platform, the lid or cover is supported on the base such that the lower surface of the lid lies vertically above and spaced from the well walls, thereby leaving small gaps.

U.S. Pat. No. 4,599,314 to Shami discloses a multiple vessel specimen tray with a lid for releasably adhering vessel covers. However, the covers are independent and separate for each vessel, that is, there is no common cover for all of the wells.

U.S. Pat. No. 4,599,315 to Terasaki et al discloses a microdroplet test apparatus in which a tray is formed with multiple wells therein. The cover has various rods which project into the wells. However, the rods do not provide a sealing action, and are only used to better optically view the contents of the wells. Further, the wells are in gaseous communication with each other.

U.S. Pat. No. 4,299,921 to Youssef discloses a prolonged incubation microbiological apparatus. However, there is only a single dish with a single chamber.

OBJECTS AND SUMMARY OF THE INVENTION

Accordingly, it is an object of the present invention to provide a crystal forming device that overcomes the problems with the aforementioned prior art.

It is another object of the present invention to provide a simple two component crystal forming device in which multiple experiments can be set-up and sealed in a minimum number of steps.

It is still another object of the present invention to provide a crystal forming device in which the number of dispensing and sealing operations are minimized.

It is yet another object of the present invention to provide a crystal forming device in which the complexity of experimental setup is reduced, while still maintaining comparable equilibration time, size and quality of crystals as in known systems.

It is a further object of the present invention to provide a crystal forming device which can be produced from a conventional coverglass-multi-well plate set-up.

It is a still further object of the present invention to provide a crystal forming device which can be used in an automated or manual system.

It is a yet further object of the present invention to provide a crystal forming device in which experiments can be viewed with a minimum of handling.

It is another object of the present invention to provide a stable, portable crystal forming device which can readily be viewed without disturbing the on-going vapor equilibration within each experiment.

In accordance with an aspect of the present invention, a crystal forming device includes a base plate having a plurality of wells therein, each well adapted to receive a reservoir solution therein and each well having a bottom and a circumferential side wall connected with the bottom to define a chamber therein, the side wall having an upper circumferential edge defining an upper opening of the well; and single removable cover means for covering all of the wells, the single removable cover means having a lower surface which rests on the upper circumferential edges of the wells to seal the wells and to thereby seal the chambers.

In accordance with another aspect of the present invention, a method of forming macromolecular crystals, includes the steps of dispensing a reservoir solution in a plurality of wells formed in a base plate, with each well having a bottom and a circumferential side wall connected with the bottom to define a chamber therein, each side wall having an upper circumferential edge defining an upper opening of the well through which the reservoir solution is dispensed; forming a plurality of droplets containing a macromolecular solution on a single cover, at positions in correspondence to the wells supplied with the reservoir solution; inverting the single cover; and positioning the inverted single cover on the upper circumferential edges so as to seal the chambers, wherein the droplets hang in a suspended state over the respective reservoir solutions.

In addition, a silicon sealing grease is preferably applied to the upper circumferential edge of each well having the reservoir solution therein, prior to positioning the inverted single cover thereon.

The above and other objects, features and advantages of the invention will become readily apparent from the following detailed description thereof which is to be read in connection with the accompanying drawings.

DETAILED DESCRIPTION OF THE PREFERRED EMBODIMENTS

Figure 1:
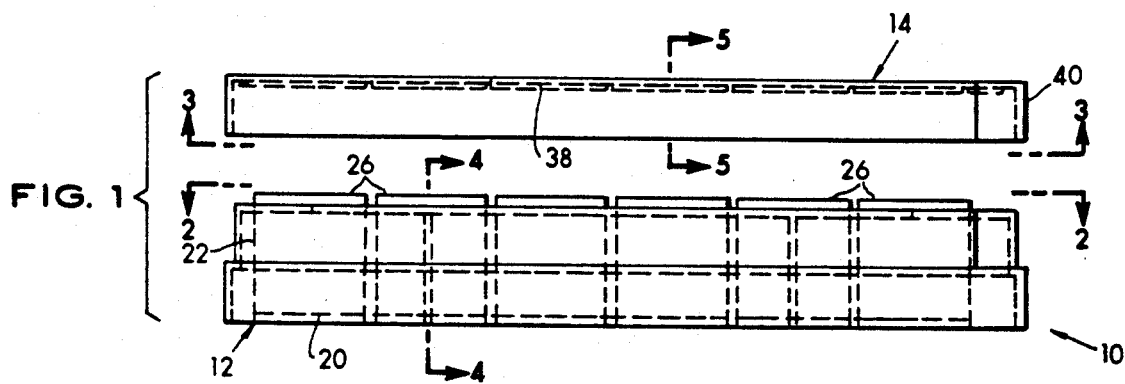
FIG. 1 is a side elevational view, partially in phantom, of a macromolecular crystal forming device according to the present invention, in exploded form.
Figure 2:
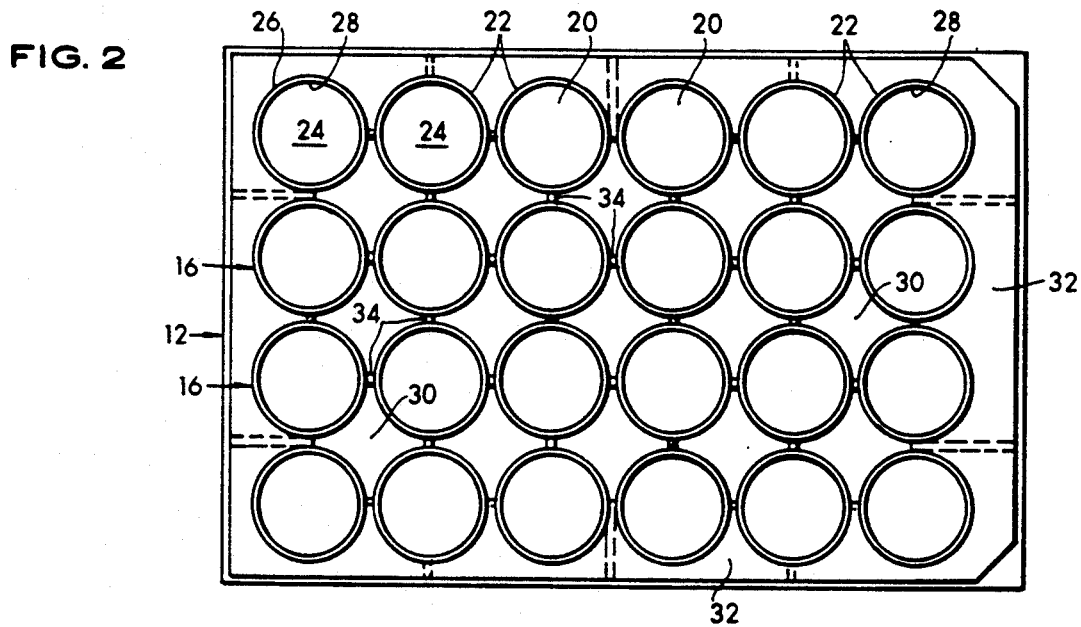
FIG. 2 is top plan view of the base plate of the crystal forming device of FIG. 1, viewed from line 2—2 thereof.
Figure 3:
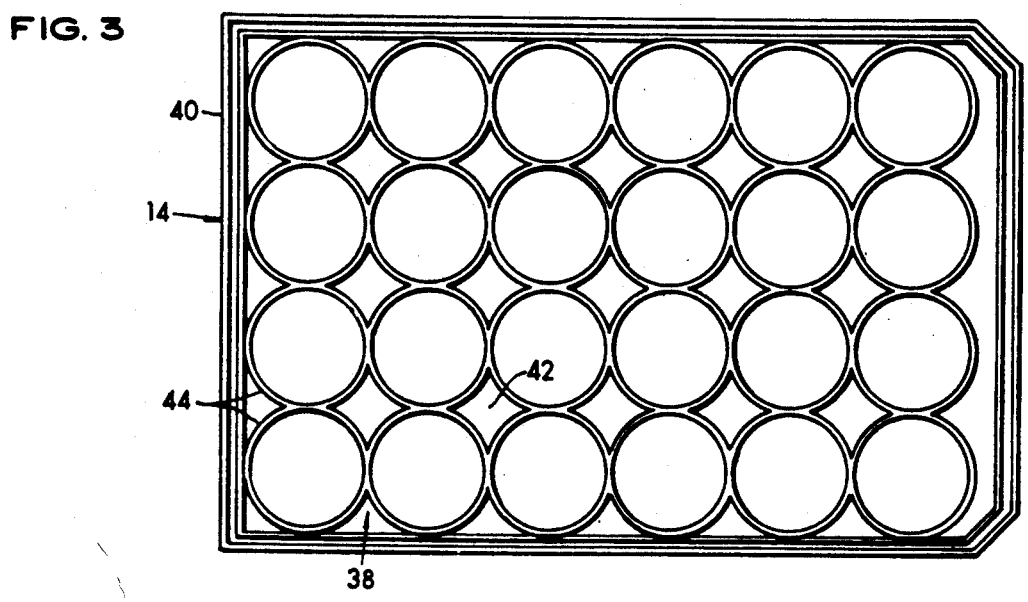
FIG. 3 is a bottom plan view of the single cover of the crystal forming device of FIG. 1, viewed from line 3—3 thereof.
Figure 4:
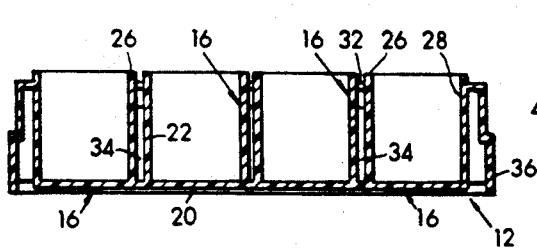
FIG. 4 is a cross-sectional view of the base plate of the crystal forming device of FIG. 1, taken along line 4—4 thereof.
Figure 5:
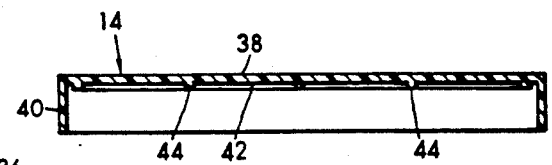
FIG. 5 is a cross-sectional view of the cover of the crystal forming device of FIG. 1, taken along line 5—5 thereof.

Referring to the drawings in detail, a crystal forming device 10 according to the present invention includes a base plate 12 and a single removable cover 14 therefor.

Specifically, base plate 12 includes a plurality of wells 16 therein, each well 16 adapted to receive a reservoir solution 18 containing a precipitating agent therein. Although twenty-four such wells 16 are shown, the present invention is not limited thereby, and this number may vary. Each well 16 has a bottom wall 20 and a cylindrical side wall 22 connected at its lower end with bottom wall 20 to define a cup-like crystallization chamber 24 therein. Only a portion of each chamber 24 is filled with reservoir solution 18. Further, the upper circular edge or rim 26 of each side wall 22 is open to define an upper opening 28 of the respective well 16.

Bottom walls 20 of wells 16 are connected together by a bottom connecting wall 30 which extends only between adjacent bottom walls 20, while upper portions of side walls 22 are connected together by a top connecting wall 32 that extends only around the periphery of side walls 22. In accordance with an important aspect of the present invention, wells 16 extend to a greater height than top connecting wall 32. In other words, upper circular edges 26 are higher than top connecting wall 32, and are also positioned in the same plane. This is important, as will be described in greater detail hereinafter, so that a single cover can rest directly on upper circular edges 26 to seal chambers 24, and thereby provide a plurality of individually sealed crystallization chambers. Finally, adjacent side walls 22 are connected together, along approximately the lower two-thirds height thereof, by tie connecting walls 34.

Further, a peripheral stepped side supporting wall 36 is connected to the peripheral edge of top connecting wall 32 and extends to a position below bottom connecting wall 30. In this manner, the lower edge of supporting wall 36 supports crystal forming device 10 on a flat surface.

Preferably, base plate 12 is made from a sturdy plastic material, such as a tissue culture treated polystyrene material of the type used to construct the FALCON 3047 MULTIWELL plate. The material used should be resistant to chemicals, such as methyl pentane diol, organic acids and alcohols, and should be stable for long term storage in pH 3-10 solutions. Polystyrene used in disposable multi-well plates is an inexpensive, widely used laboratory material for use in multiple tissue culture and assay applications. Characteristically, this material has good optical properties and has proven to be chemically resistant to the chemicals used in screening conditions for crystallization.

In addition, it is important that bottom walls 20 and side walls 22 are transparent or translucent for viewing the droplets suspended from cover plate 38 through a microscope or the like. However, bottom connecting wall 30 and top connecting wall 32 can be translucent or opaque to more clearly differentiate wells 16.

Single removable cover 14 includes a transparent flat cover plate 38 as well as a peripheral lip 40 that extends around the periphery of flat cover plate 38. Peripheral lip 40 is dimensioned so as to fit around the upper portion of supporting side wall 36. However, as shown best in FIG. 6, the height of peripheral lip 40 is sufficiently small so that the lower edge thereof does not support cover 14 on base plate 12, but rather, as will be described in detail hereinafter, cover 14 is supported on base plate 12 only by flat cover plate 38 resting on upper circular edges 26.

Although not required, the lower or inner surface 42 of cover plate 38 has a plurality of circular beads 44 formed thereon. Each bead 44 has a diameter greater than that of upper circular edges 26 of wells 16 so as to extend therearound when cover 14 is positioned on base plate 12. As will be appreciated from the discussion that follows, one function of circular beads 44 is as a template for droplets containing a macromolecular solution. This design modification greatly simplifies manual crystallization screening. Such beads 44 are of the type formed on the aforementioned FALCON 3047 MULTIWELL plate.

Preferably, the entire cover 14 is made from the same transparent polystyrene material as base plate. In addition, the inner surface 42 of flat cover plate 38 is preferably siliconized to ensure better droplet formation thereon. Specifically, to insure good droplet formation, a siliconizing agent is applied to prevent spreading of macromolecular droplets over time on cover 14. It was found that using a solution of SURFASIL siliconizing agent in hexane to pretreat the polystyrene surface of cover plate 38, effectively gave a uniform silicon film on polystyrene cover 14. Siliconized covers 14 allowed for comparable macromolecular droplet formation to that found for hanging drops from conventional siliconized coverglasses.

Figure 6:
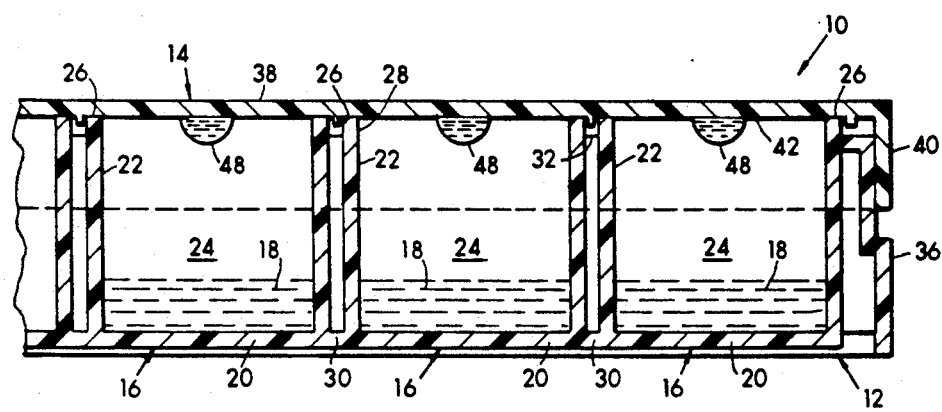
FIG. 6 is a cross-sectional view of a portion of the crystal forming device of FIG. 1 in assembled form and in use with the vapor diffusion hanging drop method.
Figure 7:
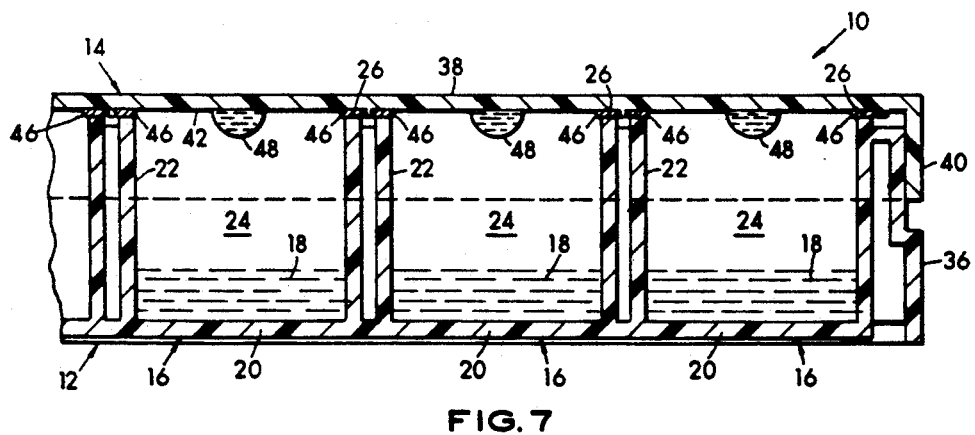
FIG. 7 is a cross-sectional view of a portion of the crystal forming device of FIG. 1 in assembled form and in use with the vapor diffusion hanging drop method, in conjunction with a silicon seal.

Although a sealing action may occur only with cover plate 38 sitting directly on upper circular edges 26, as shown in FIG. 6, a silicon or other grease seal 46 is preferably applied to upper circular edges 26 prior to positioning of cover 14 thereon, as shown in FIG. 7. In this manner, silicon seal 46 ensures a gaseous seal of chambers 24 when cover 14 is positioned on base plate 12, and works in conjunction with upper circular edges 26 and circular beads 44 to ensure such a seal. Specifically, any imperfections in the contact region around the 24 upper circular edges 26 of wells 16 of base plate 12, and cover 14, can be masked by using grease 46 as a sealant.

A straightforward procedure which requires a minimum of easy to handle steps can therefore be followed efficiently with the present invention to screen for ideal crystallization formation.

Specifically, with the present invention, wells 16 are first partially filled with a reservoir solution 18, preferably by a pipette system. A silicon grease seal 46 is then applied to upper circular edges 26 of wells 16, manually or preferably by an automated process. Then, droplets 48 containing a macromolecular solution are provided on inner surface 42 of flat cover plate 38, within each area defined by circular beads 44. Cover 14 is then inverted and positioned on upper circular edges 6. Because of silicon seal 46, chambers 24 are sealed. At this time, each droplet 48 hangs in a suspended state over its respective reservoir solution 18. The macromolecular solution in each droplet 48 is allowed to equilibrate with the respective reservoir solution 18 which contains a higher concentration of precipitating agent. Over time, water vapor diffuses from the less concentrated macromolecular solution of droplet 48 to the more concentrated reservoir solution 18 and slowly increases the concentration of macromolecule and precipitating agent within each droplet 48.

With the present invention, in actual experiments, good droplet formation was observed after siliconizing cover plate 38. In such actual experiments, the present invention was tested in side-by-side experiments with a conventional coverglass-multiwell plate in hanging drop experiments under conditions for crystallizing chicken egg white lysozyme. It was found that device 10 according to the present invention gave comparable results to the conventional method. The size and quality of the crystals produced were comparable. Also, the crystals appeared after the same equilibration time as compared to conventional experiments.

Specifically, the experiments proceeded as follows. A 5% solution (v/v) of SURFASIL siliconizing agent in hexane, was applied to inner surface 42 of cover plate 38 and permitted to dry. Inner surface 42 was polished with a lint free soft paper towel, and the surface was blown clean with a precision duster such as the precision duster sold under the trademark FISHERBRAND, to remove any dirt or dust on the surface.

Then, a known procedure for crystallizing hen chicken white lysozyme using the vapor diffusion hanging drop method, as published in M. Pursey et al, JBC, 261, pages 6524-6529 (1985), was set up. Specifically, droplets of 20 mg/ml chicken egg white lysozyme in 0.01M sodium acetate with a pH of 4.0 and 4% sodium chloride, were used. The chicken egg white lysozyme was lysozyme grade I from chicken egg white, obtained from Sigma Chemical Company of St. Louis, Mo. The sodium acetate was an anhydrous ACS reagent grade, also obtained from Sigma Chemical Company. The sodium chloride was an ACS reagent grade also obtained from Sigma Chemical Company. The droplets were equilibrated against reservoir solutions of 0.01M sodium acetate with a pH of 4.0 and 8% sodium chloride at 22° C.

Microscopic inspections were performed using a Bausch and Lomb stereo microscope at 40× magnification. Crystal and droplet diameter measurements were made with a scalar eyepiece on the Bausch and Lomb stereo microscope.

In order to compare the results of the present crystal forming device 10 side-by-side with classical hanging drop experiments, several criteria were used to compare the performance of the crystallization chambers according to the present invention.

Primarily, the ability of chambers 24 to crystallize chicken egg white lysozyme as compared to control hanging drop experiments under the same experimental conditions was tested. Experiments were set-up under identical conditions, using the same precipitating and lysozyme solutions. Twenty-four identical experiments were set up, that is, one entire plate, in both a conventional arrangement of hanging drops in a multiwell plate-coverglass arrangement and in crystallization chambers 24 according to the present invention. Liquid handling, aspiration and dispensing steps into the wells of the multi-well plates and droplets onto the cover of the present invention, or the coverglasses according to the prior art, were performed manually. Experiments were monitored by microscopic inspection at 3 days, 14 days and 30 days post set-up. The crystallization onset time (time from setup to crystal formation), crystal size (mm on edge) and number of experiments producing crystals, were monitored microscopically. The results of these experiments are shown in Table 1 as follows.

TABLE 1

| METHOD | NO. EXPERIMENTS | CRYSTAL ONSET TIME (DAYS) | CRYSTAL SIZE (MM) | NO. CRYSTALS FORMED |
|---|---|---|---|---|
| CONVENTIONAL | 24 | 3 | 0.45 | 24 |
| PRESENT INVENTION | 24 | 3 | 0.45 | 22 |

It was found that the crystallization onset time was the same for both chambers. Tetragonal crystals of comparable size and quality were observed from both set of experiments. Crystals were observed in 22 out of 24 experiments in crystallization chambers of the present invention versus 24 out of 24 in the control experiments according to the prior art.

Further, droplet diameter shrinkage over time is relative to vapor evaporation rates. Microscopic measurements of change in droplet diameter were made at regular time intervals of 3 days, 14 days and 30 days. A geometric average of droplet diameters was calculated from the measurements of all the experiments. The results of these measurements are shown in Table 2, as follows.

TABLE 2

| METHOD | NO. EXPERIMENTS | INITIAL DROPLET DIAMETER (mm) | AVERAGE DROPLET DIAMETERS POST SET-UP | | |
|---|---|---|---|---|---|
| | | | 3 DAYS (mm) | 14 DAYS (mm) | 30 DAYS (mm) |
| CONVENTIONAL | 24 | 3.9 | 3.5 | 3.5 | 3.5 |
| PRESENT INVENTION | 24 | 3.8 | 3.5 | 3.5 | 3.5 |

In both the conventional set-up and experiments set-up in accordance with the present invention, there was measurable shrinkage in all the droplets after 3 days. Thereafter, the droplet diameters stabilized out to 30 days at 22° C. incubation.

These experiments confirm that device 10 having crystallization chambers 24 according to the present invention can be used to discover conditions for macromolecular crystallization with lysozyme. The size and quality of crystals prepared with the present invention are comparable to control experiments. Thus, device 10 greatly reduces the complexity of handling and setting up macromolecular crystallization experiments. Crystallization experiments can also be set-up with the present invention, using an automated handling system. Thus, all aspirating and dispensing stops necessary for setting up crystallization experiments can be performed in a automated process. Device 10 can be handled by an articulated robotic arm, for example, a CRS Plus robot or a Zymark ZYMATE 11 robot. The present invention therefore offers distinct advantages over conventional hanging drop experiments. A minimum of handling and sealing steps is required to set-up crystallization experiments. Further, the present invention, in crystallization studies with lysozyme, gives comparable results to conventional hanging drop experiments. Experimental set-up time saved can be dedicated to screening a wider range of conditions for crystallizing macromolecules, thereby allowing greater opportunity to discover novel macromolecular crystalline forms.

Utilization of crystal forming device 10 according to the present invention provides distinct advantages over commercially available crystallization chambers, particularly with respect to ease of operation. Thus, twenty-four crystallization experiments can be setup in one operation. Further, crystal forming device 10 according to the present invention is adaptable to totally automated crystallization systems, since all steps can be automated and because device 10 can be easily manipulated by an articulated robotic arm.

Thus, device 10 provides comparable results to conventional hanging drop multi-well-coverglass experiments. Crystal forming device 10 also has good optical properties and is amenable to microscopic inspection without disturbing experiments.

It will be appreciated that various changes can be made to the present invention within the scope of the claims herein. For example, although wells 16 have been shown as a having a cylindrical configuration, they could have any other suitable configuration, such as a square cross-sectional shape. As another modification, a gasket can be used to ensure the gaseous seal of each chamber in place of silicon seal 46.

Having described specific preferred embodiments of the invention with reference to the accompanying drawings, it will be appreciated that the present invention is not limited to those precise embodiments and that various changes and modifications can be effected therein by one of ordinary skill in the art without departing from the scope or spirit of the invention as defined by the appended claims.

What is claimed is:

1. A method of forming macromolecular crystals, comprising the steps of:

dispensing a reservoir solution in a plurality of wells formed in a base plate, with each well having a bottom and a circumferential side wall connected with said bottom to define a chamber therein, each said side wall having an upper circumferential edge defining an upper opening of the well through which the reservoir solution is dispensed;

forming a plurality of droplets containing a macromolecular solution on a single cover, at positions in correspondence to said wells supplied with said reservoir solution;

inverting said single cover such that said droplets remain substantially in the same positions on the single cover; and positioning said inverted single cover on said upper circumferential edges so as to seal said chambers, with each said droplet hanging in a suspended state over the reservoir solution in a respective well.

2. A method according to claim 1, further including the step of sealing the lower surface of said single removable cover means to each said well to thereby define a plurality of sealed chambers.

3. A method according to claim 2, wherein said step of sealing includes the step of applying a sealing grease to the upper circumferential edge of each said well having said reservoir solution therein, prior to positioning said inverted single cover thereon.

4. A method according to claim 3, wherein said step of applying includes the step of applying a silicon grease to said upper circumferential edges.

5. A method according to claim 1, wherein said cover has a plurality of circumferential beads formed on the lower surface thereof, said circumferential beads corresponding in position to the upper circumferential edges of said wells, and said step of forming includes the step of forming a plurality of droplets containing a macromolecular solution on the single cover, at positions within areas defined by said circumferential beads.

6. A method according to claim 5, wherein each said circumferential bead extends in surrounding relation to a respective said upper circumferential edge when said cover is positioned on said base plate.

* * * * *